US012636394B2

(12) United States Patent
Fosburg et al.

(10) Patent No.: US 12,636,394 B2
(45) Date of Patent: May 26, 2026

(54) ATOMIZER APPARATUS AND METHODS OF USE THEREOF

(71) Applicant: HALSA HOLDINGS INC., Evergreen, CO (US)

(72) Inventors: Matthew Fosburg, Long Beach, CA (US); Jeffrey C. Fisher, Phoenix, AZ (US); Gabriel Vincent Mathews, Portland, OR (US)

(73) Assignee: HALSA HOLDINGS INC., Evergreen, CO (US)

( * ) Notice: Subject to any disclaimer, the term of this patent is extended or adjusted under 35 U.S.C. 154(b) by 376 days.

(21) Appl. No.: 18/309,198

(22) Filed: Apr. 28, 2023

(65) Prior Publication Data

US 2023/0347003 A1 Nov. 2, 2023

Related U.S. Application Data

(60) Provisional application No. 63/335,982, filed on Apr. 28, 2022.

(51) Int. Cl.
*A61L 9/013* (2006.01)
*A61L 9/14* (2006.01)

(52) U.S. Cl.
CPC ................. *A61L 9/013* (2013.01); *A61L 9/14* (2013.01)

(58) Field of Classification Search
CPC ....... A61L 9/013; A61L 9/14; A61L 2209/111
See application file for complete search history.

(56) References Cited

U.S. PATENT DOCUMENTS

D1,052,165 S * 11/2024 Fosburg ........................ D27/162
2018/0290163 A1* 10/2018 Carrozza ............. B05B 13/0278

* cited by examiner

*Primary Examiner* — Jeffrey T. Palenik
(74) *Attorney, Agent, or Firm* — ArentFox Schiff LLP

(57) ABSTRACT

An atomizer including a bulb defining a hollow cavity configured to contain a substance therein, a stem extending from the bulb, and an actuator coupled to the bulb, the actuator being actuable to expel a fragrance of the substance from the stem.

17 Claims, 12 Drawing Sheets

ATOMIZER APPARATUS AND METHODS OF USE THEREOF

CROSS REFERENCE TO RELATED APPLICATION

This application claims the benefit of U.S. Provisional Patent Application No. 63/335,982, filed Apr. 28, 2022, and hereby incorporates by reference herein the contents of the prior application in their entirety.

FIELD

This disclosure relates generally to an atomizer, and more particularly to an atomizer configured to allow a customer to view and smell a product for display or sale, such as *cannabis* flower.

BACKGROUND

*Cannabis* dispensaries generally have a variety of strains of *cannabis* available to customers. Typically, customers purchasing *cannabis* in flower form like to be able to inspect, e.g., view and/or smell a sample of the strain before purchasing. Typically, *cannabis* dispensaries provide samples of each strain in a sample container having a screened opening for visualizing and/or smelling the sample. However, such displays typically involve subsequent customers being in close proximity to one or more surfaces of the sample container that a prior customer has breathed on, touched, and placed in proximity to their mouth/nose, thereby potentially conferring the prior customer's bodily fluids, such as sweat, saliva, etc., onto the sample container. In addition, samples placed in display containers having large openings may quickly lose their potency. Therefore, it would be advantageous to develop a system for displaying, inspecting and/or smelling *cannabis* flowers that does not involve customers touching and bringing their noses/mouths into close proximity to a display area or surfaces of the sample container, while avoiding rapid loss of potency of the sample.

SUMMARY

The following aspects of the disclosure and aspects thereof are described and illustrated in conjunction with systems, tools and methods that are meant to be for purposes of example and illustration, and not limiting in scope.

In one aspect, an atomizer may include a bulb defining a hollow cavity configured to receive a substance therein, a stem extending from the bulb, and an actuator coupled to the bulb and actuable to expel a fragrance of the substance from the stem. In some aspects, the stem may include a first end extending from the bulb and a second end defining an opening. In some aspects, the second end may be flared. In some aspects, the actuator may be made of or include a resilient material. In some aspects, the actuator may be removably coupled to the bulb, such that the actuator can be removed from the bulb to facilitate filling, refilling, and/or emptying of the substance contained within the bulb. In some aspects, the bulb may include a substantially flat portion configured to support the bulb on a surface.

In another aspect, an atomizer may include a bulb defining a hollow cavity configured to contain a substance therein. The bulb has an opening through which a fragrance of the substance can be dispensed. The atomizer further includes an actuator coupled to the bulb. The actuator is actuable to expel the fragrance of the substance from the opening.

In addition to the example aspects and variations described above, further aspects and variations will become apparent by reference to the drawings and by study of the following detailed description.

BRIEF DESCRIPTION OF THE DRAWINGS

Example aspects are illustrated in the drawings. It is intended that the aspects and figures disclosed herein are to be considered illustrative rather than restrictive.

DETAILED DESCRIPTION

Figure 1:
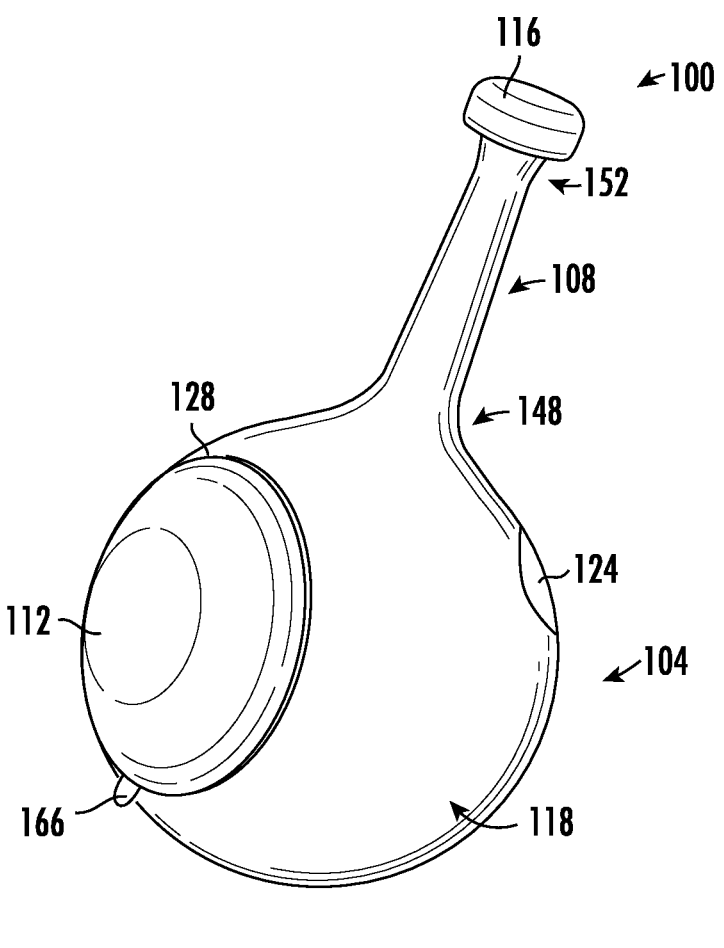
FIG. 1 illustrates a perspective view of an example atomizer, in accordance with an aspect of the disclosure.

In the following detailed description, reference is made to the accompanying figures, which form a part thereof. In the figures, similar symbols typically identify similar components, unless context dictates otherwise. The illustrative aspects described in the detailed description, figures, and claims are not meant to be limiting. Other aspects may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The following includes definitions of selected terms employed herein. The definitions include various examples and/or forms of components that fall within the scope of a term and that may be used for implementation. The examples are not intended to be limiting. Further, it will be clear to one skilled in the art that the present disclosure may be practiced without these specific details. In other instances, well-known methods, procedures, and components have not been described in detail so as to not unnecessarily obscure aspects of the present disclosure.

Throughout the disclosure, the term substantially or approximately may be used as a modifier for a geometric relationship between elements or for the shape of an element or component. While the terms substantially or approximately are not limited to a specific variation and may cover any variation that is understood by one of ordinary skill in the art to be an acceptable variation, some examples are provided as follows. In one example, the terms substantially or approximately may include a variation of less than 10% of the dimension of the object or component. In another example, the terms substantially or approximately may include a variation of less than 5% of the object or component. If the terms substantially or approximately are used to define the angular relationship of one element to another element, one non-limiting example of the terms may include a variation of 5 degrees or less. These examples are not intended to be limiting and may include variations that can be increased or decreased based on the understanding of acceptable limits to one of ordinary skill in the art.

By way of non-limiting example, aspects of the present disclosure may include an atomizer having a bulb defining a hollow cavity configured to receive a substance therein, a stem extending from the bulb, and an actuator coupled to the bulb and actuable to expel a fragrance of the substance from the stem. The bulb may include a substantially flat portion configured to support the bulb on a flat surface, for example. The atomizer may be held by a user so that the user can inspect a substance contained inside the bulb. The user may depress the actuator to expel a fragrance of the substance from the stem. In some aspects, the substance may be *cannabis* flower. The atomizer may be sized so that the user can hold the atomizer with one hand while depressing the actuator to expel the fragrance of the substance from the atomizer with the same hand. Alternatively, the user can hold the atomizer with one hand while depressing the actuator with the other hand.

Figure 2:
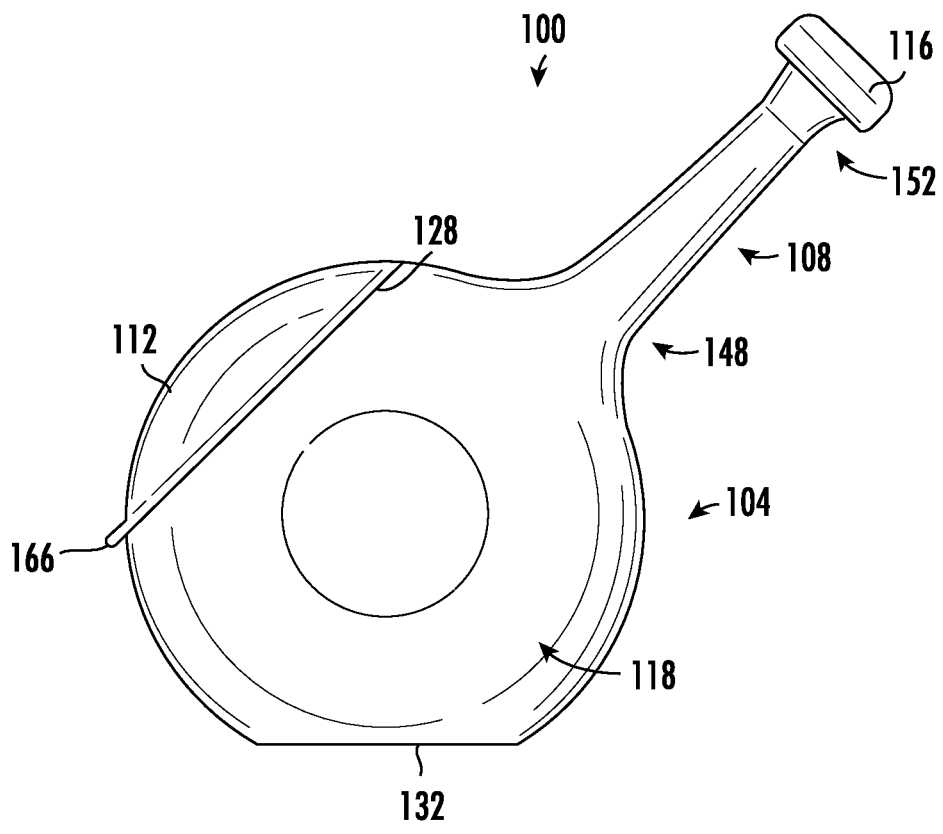
FIG. 2 illustrates a side view of the atomizer shown in FIG. 1, in accordance with an aspect of the disclosure.
Figure 3:
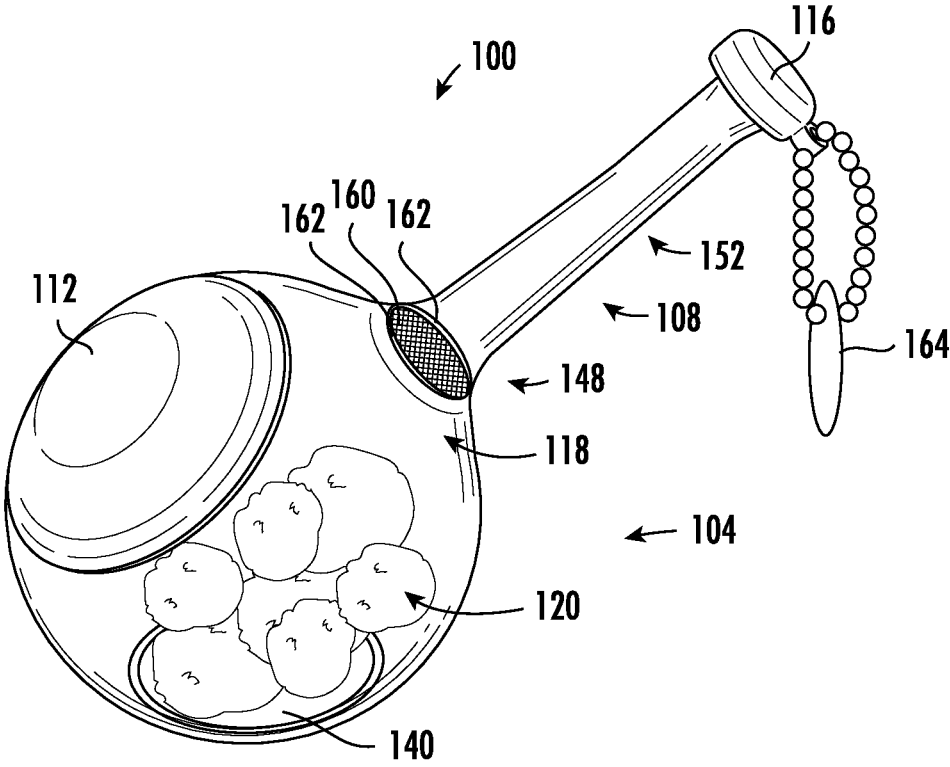
FIG. 3 illustrates a side view of the atomizer shown in FIG. 1 filled with a substance, in accordance with an aspect of the disclosure.

FIGS. 1-3 illustrate an example atomizer 100 according to an aspect of the present disclosure. The atomizer 100 may include a bulb 104, a stem 108, an actuator 112, and an optional cap 116. The bulb 104 may define a hollow cavity 118 configured to receive a substance 120 (FIGS. 3, 4) therein. Typically, the substance 120 may be a fragrant product. In some aspects, the substance 120 may be *cannabis* flower. At least a portion of the bulb 104 may be transparent, allowing the substance 120 to be visualized therethrough. In some aspects, the bulb 104 may include a magnification element 124 (FIG. 1) to allow details of the substance 120 to be viewed/visually inspected. In aspects in which the substance 120 is *cannabis* flower, the user may use the magnification element 124 to inspect tricombs on the flower. The bulb 104 may include an opening 128 therein (interchangeably referred to as a "hole" herein) configured to receive the actuator 112. In some aspects, the opening or hole 128 may be circular. In other aspects, the opening or hole 128 may have a different cross-sectional shape, such as an oval, a square, a rectangle, a hexagon, and other geometric shapes.

Figure 4:
FIG. 4 illustrates a perspective view of two of the atomizers of FIG. 1 in accordance with an aspect of the disclosure.

In some aspects, a portion 132 of the bulb 104 may be flat, so that the atomizer 100 can rest on a surface 136, such as a table, shelf, or tray (FIG. 4). In some aspects, the flat portion 132 may be positioned so that the stem 108 is angled relative to the surface 136, as shown for example in FIG. 1. In some aspects, the flat portion 132 may be positioned so that the stem 108 is substantially perpendicular to the surface 136. In some aspects, the flat portion 132 may be positioned so that the actuator 112 is positioned proximate a top of the bulb 104, as shown for example in atomizer 100 in FIG. 4. FIG. 4 also illustrates another aspect of atomizer 100' in which the flat portion 132 may be positioned so that the actuator 112' is positioned on a side of the bulb 104'. The atomizer 100' is substantially similar to the atomizer 100 except for the locations of the flat portion 132', the actuator 112', and the shape of the cap 116'.

Figure 5:
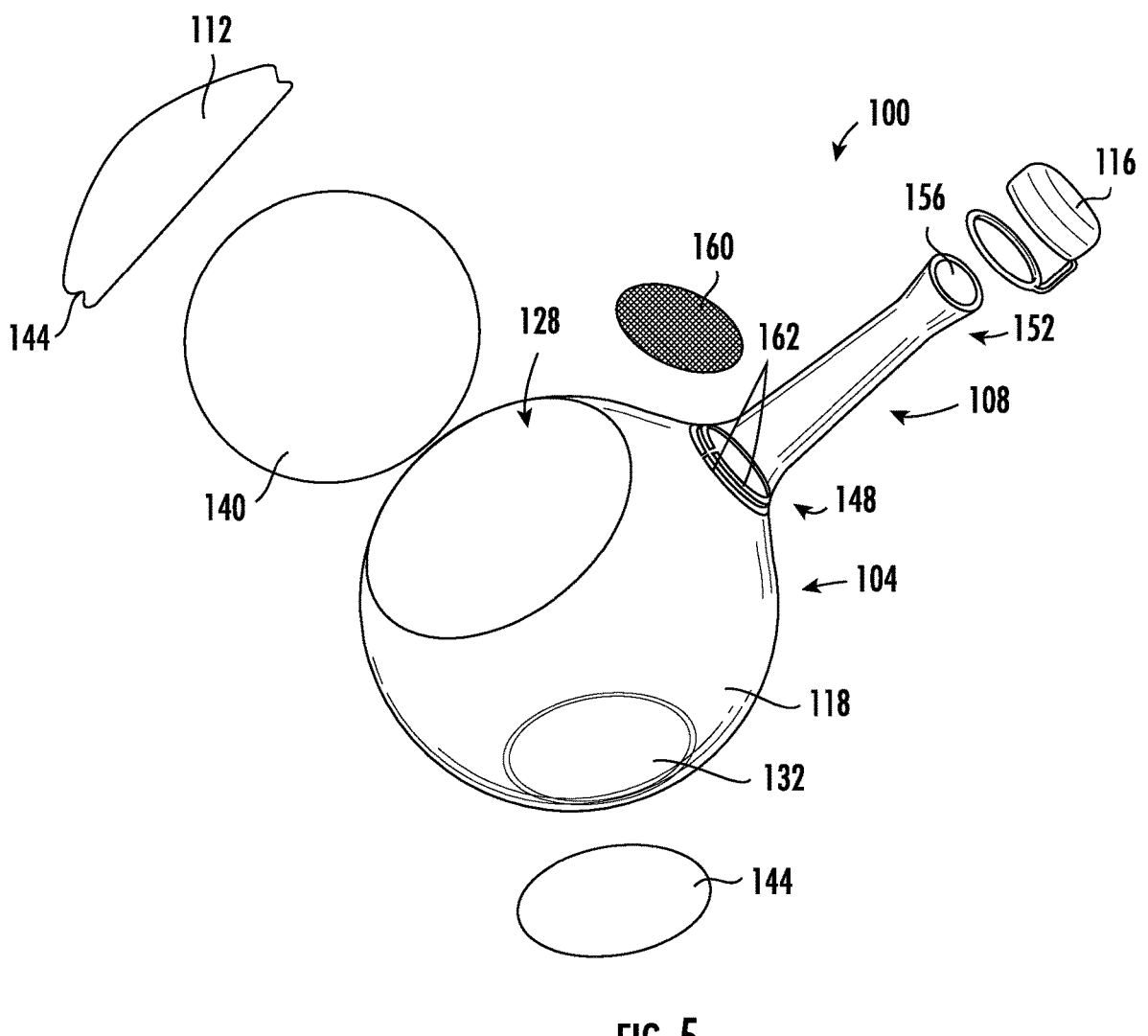
FIG. 5 illustrates an exploded view of the atomizer of FIG. 1 in accordance with an aspect of the disclosure.
Figure 6:
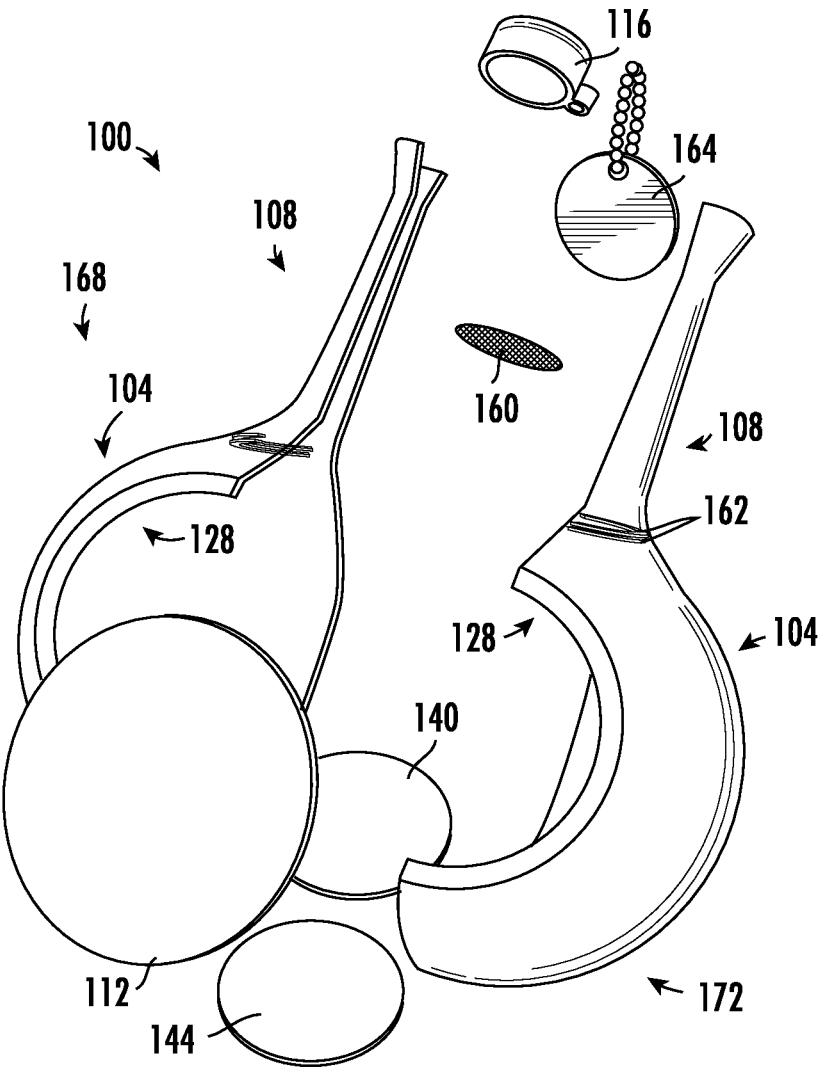
FIG. 6 illustrates another exploded view of the atomizer of FIG. 1 in accordance with an aspect of the disclosure.

As is best shown in FIGS. 3, 5, and 6, in some aspects, the bulb 104 may include a humidity control device 140. The humidity control device 140 may be configured to add or reduce humidity from the cavity 118 of the bulb 104. In some aspects, the humidity control device 140 may be a Boost® pack manufactured by Integra Specialty Products of Las Vegas, Nevada.

In some aspects, a metallic component 144 (FIGS. 5-6) may be coupled to the flat portion 132. As described in greater detail below, the metallic component 144 may allow the atomizer 100 to be secured to the surface 136 by one or more magnets.

The stem 108 may be substantially hollow and include a first end 148 and a second end 152. The first end 148 may extend from the bulb 104. The hollow interior of the stem 108 may be continuous with the hollow cavity 118 of the bulb 104. In some aspects, the first end 148 may be curved. The second end 152 may define an opening 156 (FIG. 5) through which the fragrance of the substance 120 may be dispensed. In some aspects, the second end 152 may be flared.

In some aspects, a screen 160 (FIGS. 3, 5-6) may be positioned between the portion of the hollow cavity 118 defined by the bulb 104 and the portion of the hollow cavity 118 defined by the stem 108. The screen 160 may be configured to prevent the substance 120 in the bulb 104 from entering the stem 108. Grooves 162 (FIGS. 3, 5-6) formed on an interior of the bulb 104 and/or the stem 108 may be configured to secure the screen 160.

In aspects that include the cap 116, the cap 116 may be configured to engage the second end 136 of the stem 108. In some aspects, the cap 116 may be configured to engage an exterior surface of the second end 152, as shown, for example, in FIGS. 1-3 and the atomizer 100 in FIG. 4. In some aspects, the cap 116' may be received within the opening 156', as shown for example in the atomizer 100' of FIG. 4. In some aspects, the cap 116 may be made of or include a resilient material. In some aspects, a tag 164 may be coupled to the cap 116. The tag 164 may provide information indicative of an identity of the substance 120.

The actuator 112 may be removably coupled to the portion of the bulb 104 surrounding the hole 128. In some aspects, the actuator 112 may include a groove 144 configured to receive a portion of the bulb 104 surrounding the hole 128 therein. The actuator 112 may be made of or include a resilient deformable material. This may allow the actuator 112 to be friction-fit into the hole 128 when the atomizer 100 is in a closed, or dispensing, configuration and removed from the hole 128 when the atomizer 100 is in an open, or refilling configuration. In some aspects, the actuator 112 may include a tab 166 to facilitate removal of the actuator 112 from the hole 128.

The actuator 112 may be squeezed or depressed to push air from the bulb 104 through the opening 156, allowing a fragrance of the substance 120 to pass through the opening 156. In some aspects, the bulb 104 may include an air intake vent configured to draw air into the cavity 118 as air may be expelled from the cavity 118 by the actuator 112. The atomizer 100 may therefore allow a customer to smell the substance 120 while still being at a distance from the stem 108 and the substance 120, not directly handling the substance 120, and so forth, while avoiding rapid loss of potence of the substance 120. The flared second end 152 of the stem 108 may facilitate dispersal of the fragrance of the substance 120 in the air. In some aspects, the actuator 112 may include a logo or other decorative designs. In some aspects, the actuator 112 may be curved such that the actuator 112 forms a substantially continuous surface with the exterior surface of the bulb 104. In some aspects, the atomizer 100 may be sized so that the user can hold the atomizer 100 with one hand while depressing the actuator 112 to expel the fragrance of the substance 120 from the atomizer 100 with the same hand. Alternatively, the user can hold the atomizer 100 with one hand while depressing the actuator 112 with the other hand.

FIG. 5 illustrates an exploded view of the atomizer 100 according to an aspect of the present disclosure. As shown in FIG. 5, in some aspects, the bulb 104 and the stem 108 may be manufactured as a single component. In some aspects, the atomizer 100 may be made from a glass material. In other aspects, the atomizer 100 may be made from a different material, such as plastic, for example.

FIG. 6 illustrates an exploded view of the atomizer 100 according to an aspect of the present disclosure. As shown in FIG. 6, in some aspects, the atomizer 100 may be manufactured in a first half 168 and a second half 172. In such aspects, the first half 168 and the second half 172 may be glued or otherwise affixed together. In some aspects, the atomizer 100 may be made from a glass material. In other aspects, the atomizer 100 may be made from a different material, such as plastic, for example.

Referring again to FIG. 4, in some aspects, the atomizer 100 may be used with a shelf or tray 136. In such aspects, the tray 136 may include one or more recesses 176 configured to receive the flat portion 132 therein. One or more magnets 180 may be positioned in each of the one or more recesses 176. The magnets 180 may be configured to engage the metallic component 144 to releasably secure the atomizer 100 to a particular recess 176. In some aspects, the tray 136 may include one or more QR codes disposed thereon. The QR codes can be accessed by a customer's mobile device to receive information indicative of characteristics of the substance 120, such as a strain of the substance 120, a composition of the substance 120, a harvest date of the substance 120, a flavor profile 120 of the substance, and so forth. In other aspects, the QR code may be disposed on the atomizer 100, for example on the flat portion 132 of the atomizer 100 or on the tag 164, among other locations on the atomizer 100. In aspects in which the substance 120 is *cannabis*, the information indicative of the composition of the substance 120 may include information such as a weight percentage of terpenes in the *cannabis*, a weight percentage of tetrahydrocannabinol (THC) in the *cannabis*, and so forth.

In operation, a user may pick up the atomizer 100 and examine the substance 120 therein. The user may remove the cap 115 from the atomizer 100 and squeeze or depress the actuator 112 to expel a fragrance of the substance 120 through the opening 156. The user may breathe in the fragrance without directly handling the substance 120, putting a sample container with the substance 120 in close proximity to their nose, and so forth.

To fill or refill the bulb 104, a user may remove the actuator 112 from the hole 128. The user may fill or refill the bulb 104 with the substance 120 or empty the bulb 104 via the hole 128. The user may then replace the actuator 112 in the hole 128.

Figure 7:
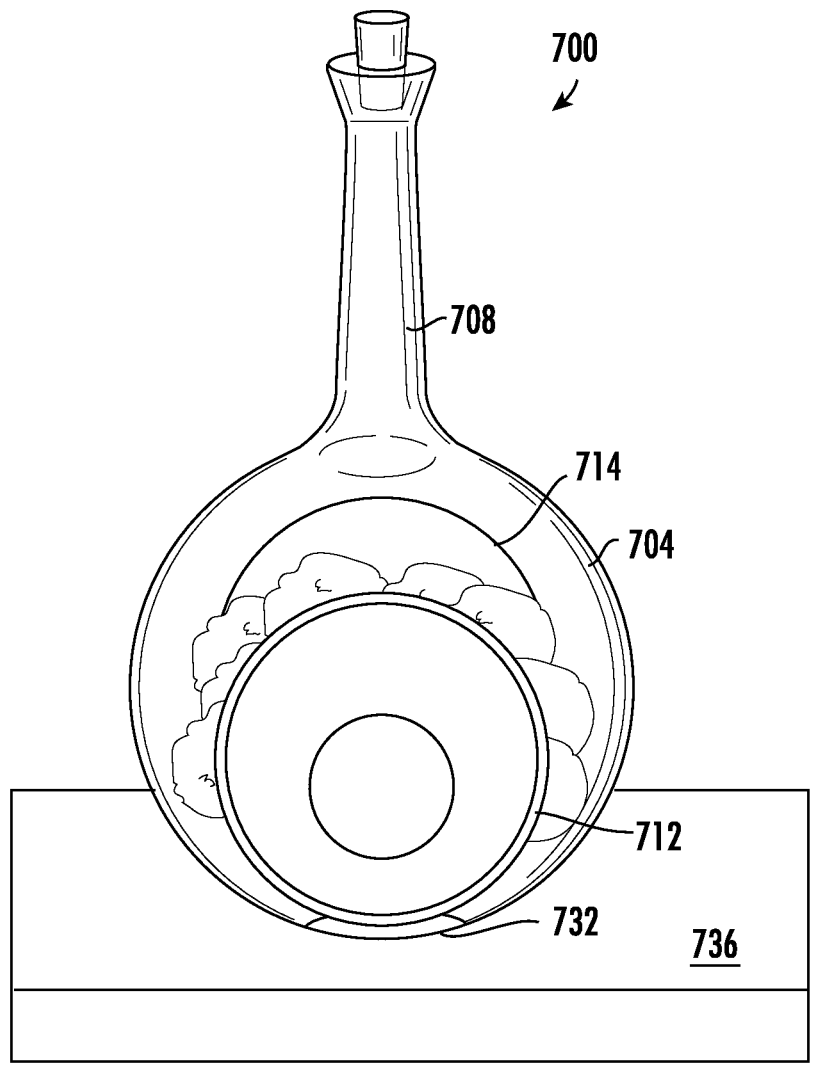
FIG. 7 illustrates a perspective view of an example atomizer, in accordance with another aspect of the disclosure.
Figure 8:
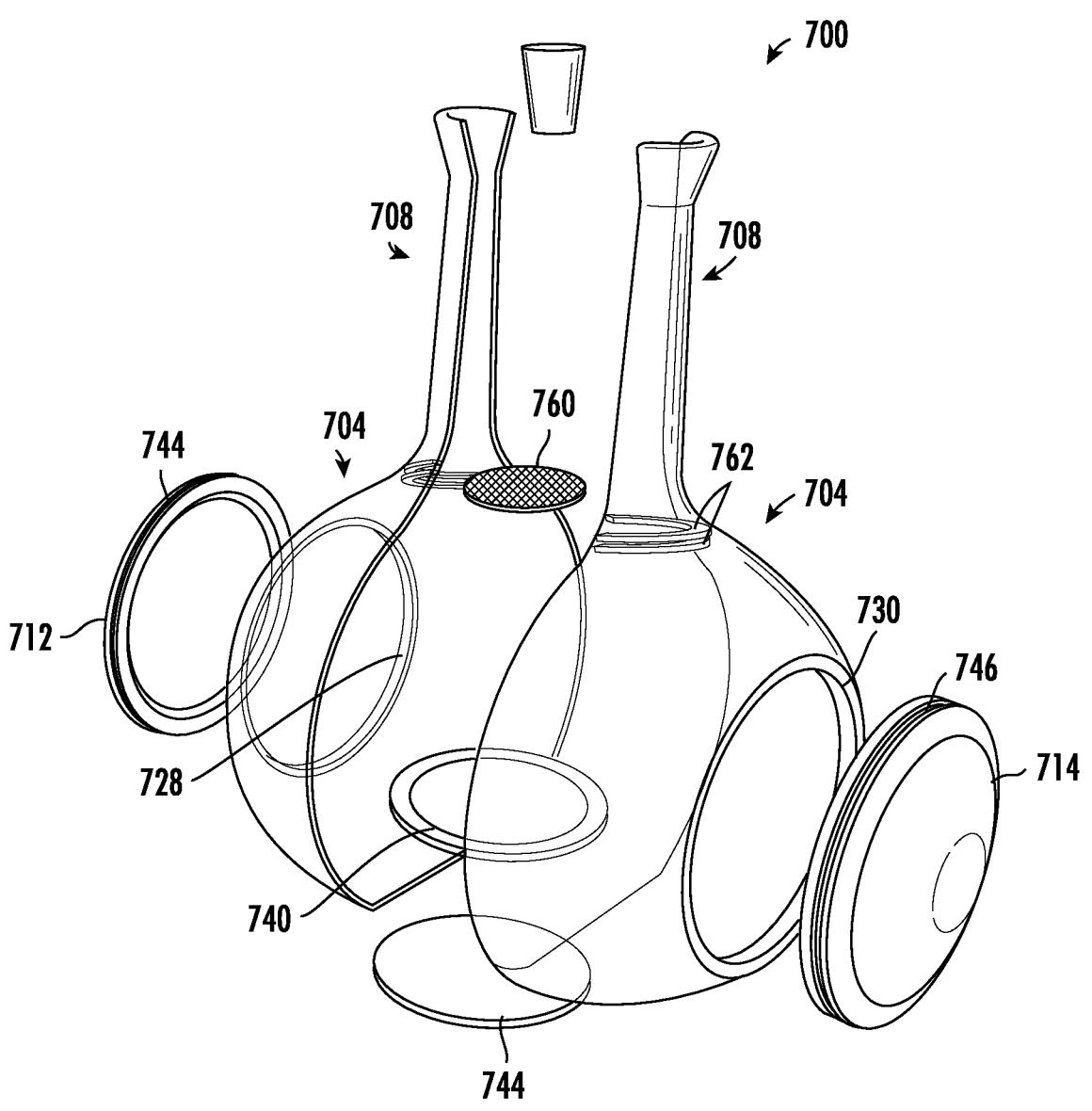
FIG. 8 illustrates an exploded view of the atomizer of FIG. 7 in accordance with an aspect of the disclosure.

FIGS. 7-8 illustrate further aspects of another example atomizer 700 according to aspects of the present disclosure. Like parts between the atomizer 100 of FIGS. 1-6 and the atomizer 700 of FIGS. 7-8 are described using similar numbers. Similar corresponding aspects of the atomizer 700 to those already described for the atomizer 100 are omitted for brevity.

As shown in FIG. 7, the atomizer 700 may include a first actuator 712 and a second actuator 714. Both the first and second actuators 712, 714 may be substantially similar to the actuator 112 described above. The first and second actuators 712, 714 may be removably coupled to the bulb 704, similar to the description above with regard to the actuator 112. In some aspects, the first and second actuators 712, 714 may be diametrically opposed. In some aspects, a flat portion 732 of the bulb 704 may be positioned so that the stem 708 is substantially perpendicular to a surface 736, as shown for example in FIG. 7. In some aspects, the flat portion 732 of the bulb 704 may be positioned so that so that the stem 708 is angled relative to the surface 736.

FIG. 8 illustrates an exploded view of the atomizer 700. As shown in FIG. 8, the atomizer 700 may include a first hole 728 configured to receive the first actuator 712 and a second hole 730 configured to receive the second actuator 714. Each of the actuators 712, 714 may include a groove 744, 746, respectively. The grooves 744, 746 may be configured to receive a portion of the bulb 704 surrounding the holes 728, 730 therein, respectively. In some aspects, the holes 728, 730 may be circular. In other aspects, the holes 728, 730 may have a different cross-sectional shape, such as an oval, a square, a rectangle, a hexagon, and other geometric shapes.

Figure 9:
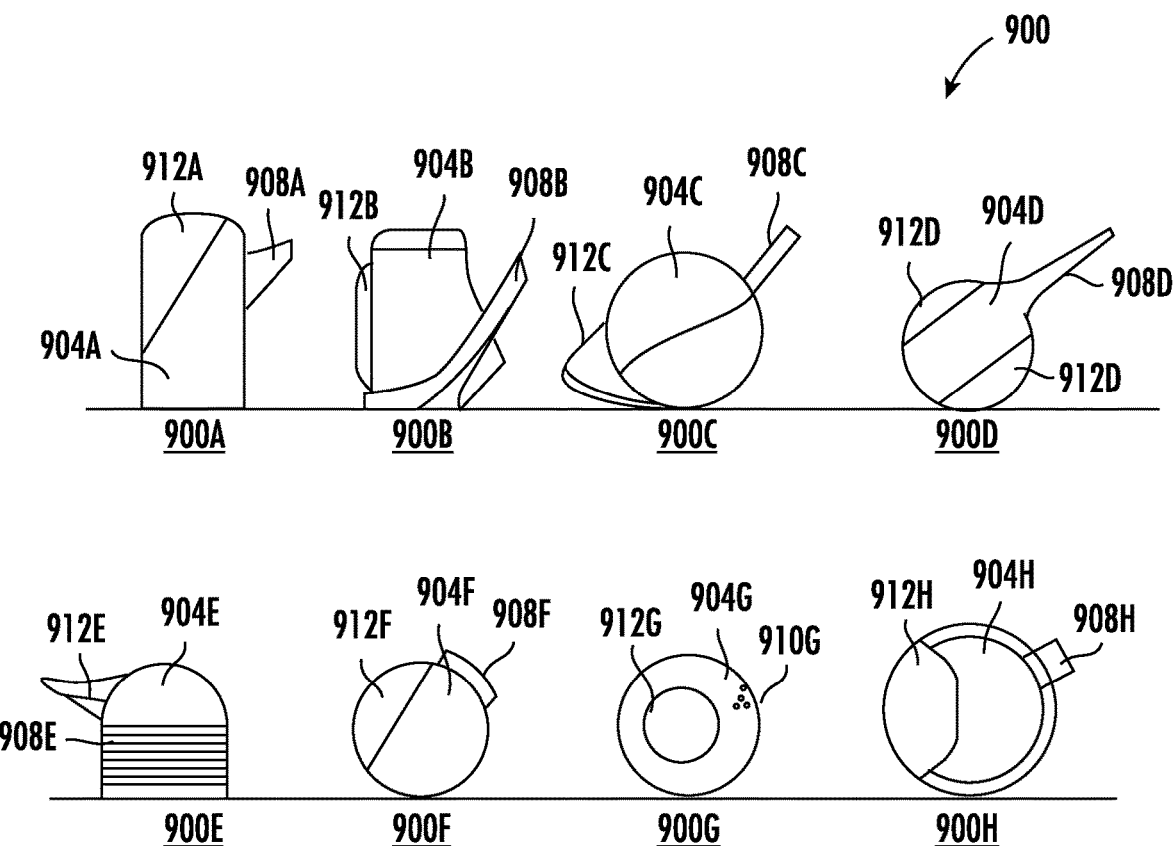
FIG. 9 illustrates a group of atomizers in accordance with aspects of the disclosure.

FIG. 9 illustrates a group 900 of atomizers 900A-900H. Like parts between the atomizer 100 of FIGS. 1-6 and the atomizers 900A-900H of FIG. 9 are described using similar numbers. Similar corresponding aspects of the atomizers 900A-900H to those already described for the atomizer 100 are omitted for brevity.

Each of the atomizers 900A-900H each may include a bulb 904A-904H configured to receive a substance therein and an actuator 912A-912H that may be made of or include a resiliently deformable material. The atomizers 900A-900F and 900H each include a stem 908A-908F and 908H. The actuators 912A-912F and 912H may be squeezed and/or depressed to release a fragrance of the substance through the stems 908A-908F and 908H. The bulb 904G of the atomizer 900G may include a plurality of openings 910G. The actuator 912G may be squeezed and/or depressed to release a fragrance of the substance through the openings 956G.

Figure 10:
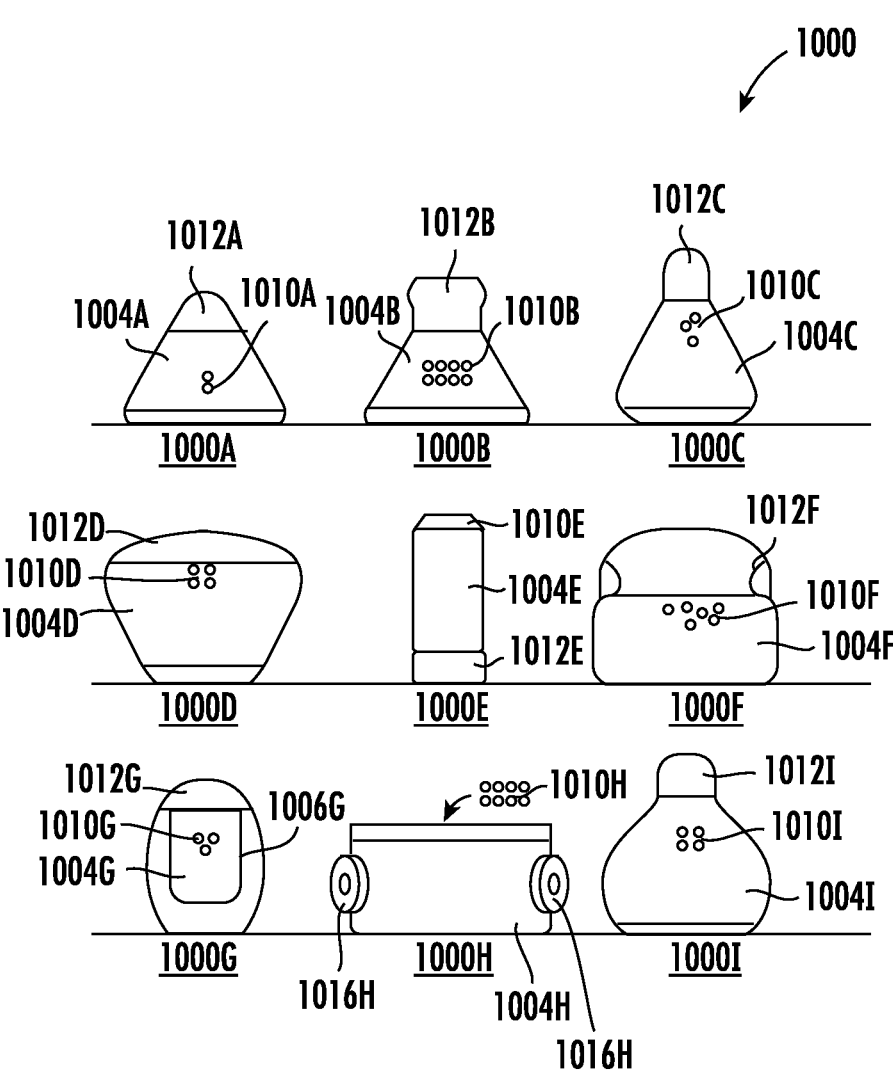
FIG. 10 illustrates another group of atomizers in accordance with aspects of the disclosure.

FIG. 10 illustrates a group 1000 of atomizers 1000A-1000I. Like parts between the atomizer 100 of FIGS. 1-6 and the atomizers 1000A-1000I of FIG. 10 are described using similar numbers. Similar corresponding aspects of the atomizers 1000A-1000I to those already described for the atomizer 100 are omitted for brevity.

Each of the atomizers 1000A-1000I may include a vessel or bulb 1004A-1004I configured to receive a substance therein and an actuator 1012A-1012I that may be or include a resiliently deformable material. Each of the bulbs 1004A-1004I may include a plurality of openings 1010A-1010I. The actuators 1012A-1012I may be squeezed and/or depressed to release a fragrance of the substance through the openings 1056A-1056I. In some aspects, such as in the variant 1000G, the bulb 1004G may be double-walled. In such aspects, a vacuum may be present between the two walls 1006G. The double-walled bulb 1004G may provide thermal insulation for the substance contained in the bulb 1004G.

Figure 11:
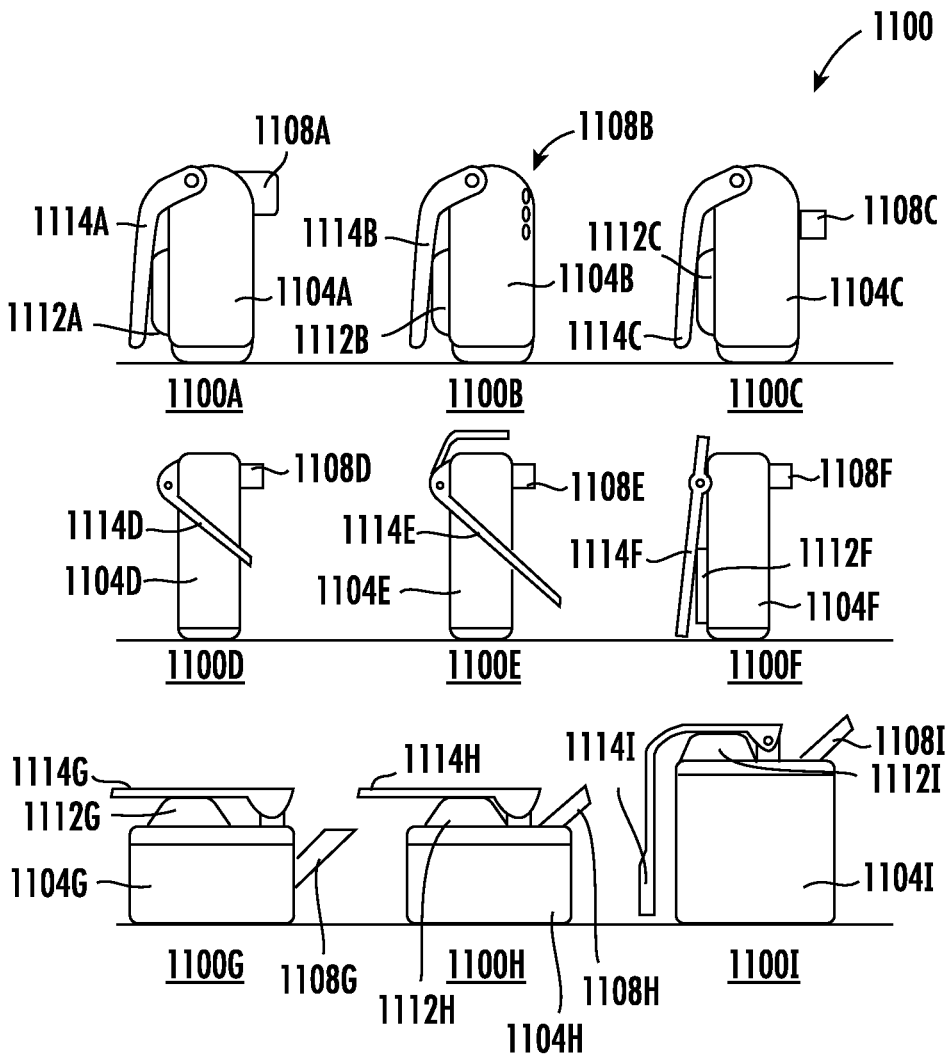
FIG. 11 illustrates yet another group of atomizers in accordance with aspects of the disclosure.

FIG. 11 illustrates a group 1100 of atomizers 1100A-1100I. Like parts between the atomizer 100 of FIGS. 1-6 and the atomizers 1100A-1100I of FIG. 11 are described using similar numbers. Similar corresponding aspects of the atomizers 1100A-1100I to those already described for the atomizer 100 are omitted for brevity.

Each of the atomizers 1100A-1100I may include a vessel or bulb 1104A-1104I configured to receive a substance therein. The atomizers 1100A and 1100C-1100I may each include a stem 1108A, 1108C-1108I, respectively. The atomizer 1100B may include a plurality of openings 1110B in the bulb 1104B. A fragrance of the substance contained within the bulbs 1104A-1104I may be dispensed through the stems 1108A, 1108C-1108I, and/or the openings 1110B.

As shown in FIG. 11, the atomizers 1100A-1100C and 1100F-1100I each may include an actuator 1112A-1112C and 1112F-1112I, respectively, that may be made of or include a resiliently deformable material. Each of the actuators 1112A-1112C and 1112F-1112I may be actuated by levers 1114A-1114C and 1114F-1114I, respectively. To dispense a fragrance of a substance contained in the bulbs 1104A-1104C and 1104F-1104I, the levers 1114A-1114C and 1114F-1114I may be pushed toward the bulbs 1104A-1104C and 1104F-1104I, respectively, thereby compressing the actuators 1112A-1112C and 1112F-1112I against the respective bulbs 1104A-1104C and 1104F-1112I, causing fragrant air to be dispensed from the bulbs 1104A-1104C and 1104F-1112I.

The atomizers 1100D and 1100E may not include actuators similar to the actuators 1112A-1112C and 1112F-1112I shown in FIG. 11 (e.g., the atomizers 1100A-1100C and 1100F-1100I). Instead, to dispense a fragrance of a substance contained in the bulbs 1104D, 1104F, the levers 1114D, 1114E may be pushed toward the bulbs 1104D, 1104E, causing fragrant air to be dispensed from the bulbs 1104E, 1104D.

Figure 12:
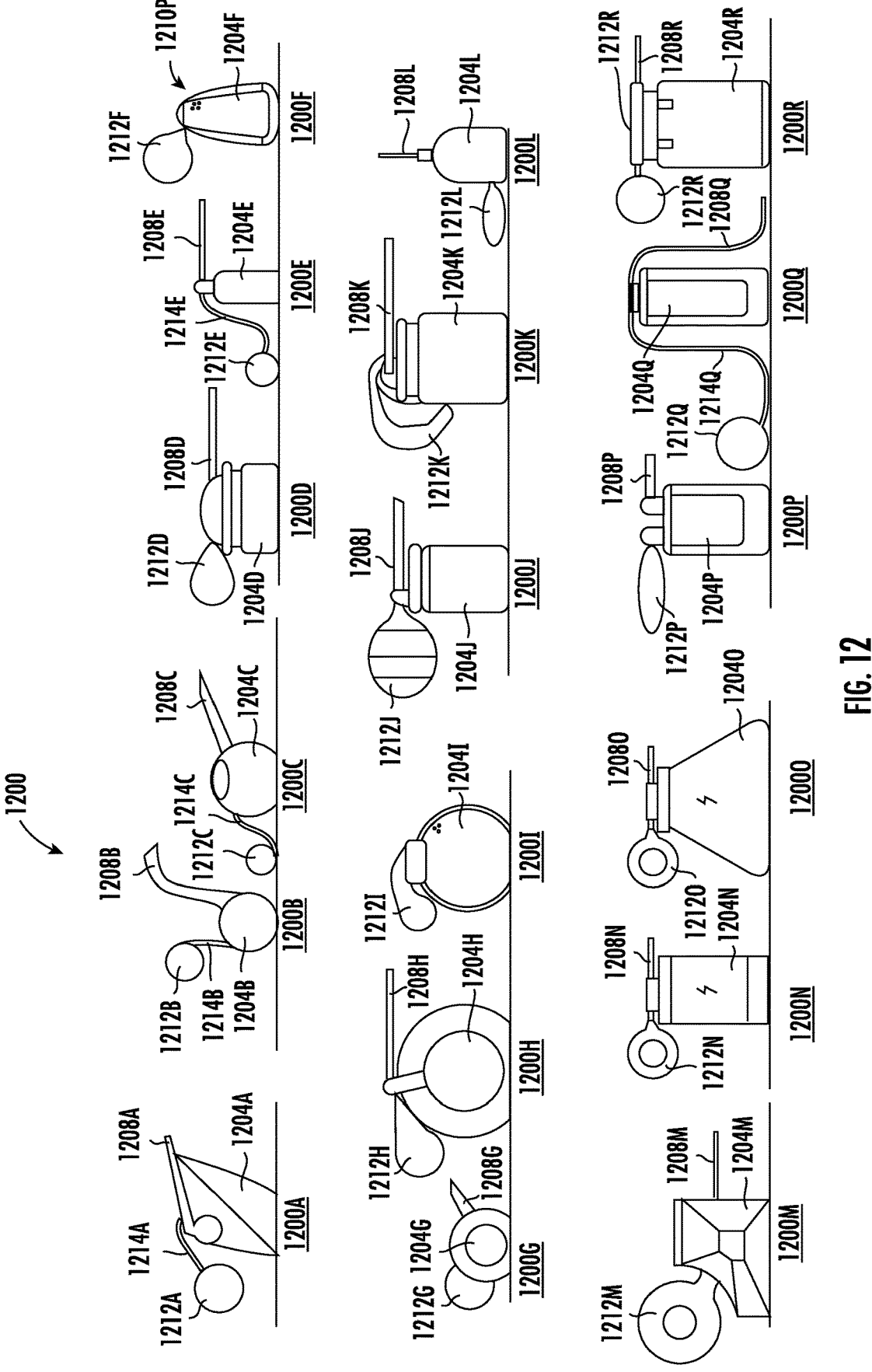
FIG. 12 illustrates yet another group of atomizers in accordance with aspects of the disclosure.

FIG. 12 illustrates a group 1200 of atomizers 1200A-1200R. Like parts between the atomizer 100 of FIGS. 1-6 and the atomizers 1200A-1200R of FIG. 12 are described using similar numbers. Similar corresponding aspects of the atomizers 1200A-1200R to those already described for the atomizer 100 are omitted for brevity.

Each of the atomizers 1200A-1200R may include a vessel or bulb 1204A-1204R configured to receive a substance therein. In some aspects, such as in the variants 1200F, 1200G, 1200I, 1200L, 1200P, and 1200Q, the bulbs 1204F, 1204G, 1204I, 1204L, 1204P, and 1204Q may be double-walled. In such aspects, a vacuum may be present between the two walls. The double-walled bulbs 1204F, 1204G, 1204I, 1204L, 1204P, and 1204Q may provide thermal insulation for the substance contained in the bulbs 1204F, 1204G, 1204I, 1204L, 1204P, and 1204Q.

Each of the atomizers 1200A-1200R may include an actuator 1212A-1212R that may be made of or include a resiliently deformable material. As shown in FIG. 12, the atomizers 1212A-1212R may protrude from the bulbs 1204A-1204R (e.g., may not lie flush with a perimeter of the bulbs 1204A-1204R). The actuators 1212A-1212R may be substantially spherical-shaped, substantially tear-drop shaped, substantially tubular-shaped, or ring-shaped, or have a non-geometric shape. In some aspects, the actuator may be directly coupled to the bulb, as shown for example with respect to the actuators 1212D, and 1212F-1212P and the bulbs 1204D and 1204F-1204P, respectively. In some aspects, the actuator may be indirectly coupled to the bulb, for example by tubing. This is shown for example with respect to the actuators 1212A-1212C, 1212E, 1212Q, and 1212R, the tubing 1214A-1214C, 1214E, 1214Q, and 1214R, and the bulbs 1204A-1204C, 1204E, 1204Q, and 1204R, respectively.

The actuators 1212A-1212R may be squeezed and/or depressed to release a fragrance of the substance through stems or openings of the atomizers 1200A-1200R.

The atomizers 1200A-1200E, 1200G-1200H, and 1200K-1200M may each include a stem 1208A-1208E, 1208G-1208H, and 1208K-1208M, respectively. Actuation of the actuators 1212A-1212E, 1212G-1212H, and 1212K-1212M may dispense a fragrance of a substance contained within the bulbs 1204A-1204E, 1204G-1204H, and 1204K-1204M though the stems 1208A-1208E, 1208G-1208H, and 1208K-1208M, respectively. The stems 1208A-1208E, 1208G-1208H, and 1208K-1208M may have a variety of shapes. For example, the stems 1208A-1208E, 1208G-1208H, and 1208K-1208M may be straight, curved, tapered, needle-shaped, tubular, and so forth.

The atomizers 1200F and 1200I may each include a plurality of openings 1210F, 1210I in the bulbs 1204F, 1204I, respectively. The actuators 1212F, 1212I may be squeezed and/or depressed to release a fragrance of the substance contained within the bulbs 1204F, 1204I through the openings 1210F, 1210I.

While a number of example aspects and aspects have been discussed above, those of skill in the art will recognize that still further modifications, permutations, additions and sub-combinations thereof of the features of the disclosed aspects are still possible. It is therefore intended that the following appended claims and claims hereafter introduced are interpreted to include all such modifications, permutations, additions and sub-combinations as are within their true spirit and scope.

What is claimed is:

1. An atomizer comprising:
a bulb defining a hollow cavity configured to contain a substance therein;
a stem extending from the bulb;
an actuator constructed of a resilient material and coupled to the bulb, the actuator being actuable to expel a fragrance of the substance from the stem; and
a screen positioned between a portion of the hollow cavity defined by the bulb and a portion of the hollow cavity defined by the stem.

2. The atomizer of claim 1, wherein the stem includes a first end extending from the bulb and as second end defining an opening, and wherein the second end is flared.

3. The atomizer of claim 1, wherein the actuator is removably coupled to the bulb.

4. The atomizer of claim 3, wherein the substance can be added to or removed from the hollow cavity when the actuator is removed from the bulb.

5. The atomizer of claim 1, wherein the bulb includes a substantially flat portion configured to support the bulb on a surface in a configuration in which the stem is angled relative to the surface.

6. The atomizer of claim 1, wherein the bulb includes a substantially flat portion configured to support the bulb on a surface in a configuration in which the stem is oriented substantially perpendicular to the surface.

7. The atomizer of claim 1, wherein the actuator is a first actuator, and further comprising a second actuator coupled to the bulb, the second actuator being actuable to expel a fragrance of the substance from the stem.

8. The atomizer of claim 1, wherein a humidity control device is positioned within the hollow cavity.

9. The atomizer of claim 1, wherein the bulb is formed as a single piece.

10. An atomizer, a bulb defining a hollow cavity configured to contain a substance therein, the bulb having an opening through which a fragrance of the substance can be dispensed;

and an actuator constructed of a resilient, deformable material and coupled to the bulb, the actuator being actuable to expel the fragrance of the substance from the opening, wherein the bulb includes a magnification element.

11. The atomizer of claim 10, wherein the opening is formed in a stem extending from the bulb.

12. The atomizer of claim 10, wherein the opening is one hole of a plurality of holes.

13. The atomizer of claim 10, wherein the opening is a first opening and wherein the bulb includes a second opening and the actuator is removably coupled to the second opening.

14. The atomizer of claim 13, wherein the hollow cavity can be filled or refilled with the substance when the actuator is removed from the second opening.

15. The atomizer of claim 13, wherein the actuator is friction fit into the second opening.

16. The atomizer of claim 10, wherein the resilient, deformable material is configured to be squeezed or depressed to expel the fragrance of the substance from the opening.

17. The atomizer of claim 10, wherein the actuator forms a substantially continuous surface with an exterior surface of the bulb.

* * * * *